(12) United States Patent
Schreiber et al.

(10) Patent No.: US 10,401,290 B2
(45) Date of Patent: Sep. 3, 2019

(54) CIRCUIT, SYSTEM AND METHOD FOR SUPPRESSING A SPURIOUS PULSE IN A MEASUREMENT SIGNAL

(71) Applicant: Leica Microsystems CMS GmbH, Wetzlar (DE)

(72) Inventors: Frank Schreiber, Bad Urach (DE); Patric Mrawek, Neustadt (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 211 days.

(21) Appl. No.: 15/673,437

(22) Filed: Aug. 10, 2017

(65) Prior Publication Data
US 2018/0045647 A1    Feb. 15, 2018

(30) Foreign Application Priority Data
Aug. 12, 2016    (LU) .......................................... 93176

(51) Int. Cl.
*H03K 3/013*    (2006.01)
*G01N 21/64*    (2006.01)
*G02B 21/16*    (2006.01)

(52) U.S. Cl.
CPC ......... *G01N 21/6458* (2013.01); *G02B 21/16* (2013.01); *G01N 2201/12* (2013.01)

(58) Field of Classification Search
CPC ........... G01N 21/6458; G01N 2201/12; G02B 21/16; G01R 23/02; H03K 3/013; H03K 3/03
USPC ...................................................... 250/214 R
See application file for complete search history.

(56) References Cited

U.S. PATENT DOCUMENTS 4,073,432 A * 2/1978 Schroder ................ G01R 23/02
324/76.61

* cited by examiner

*Primary Examiner* — Que Tan Le
(74) *Attorney, Agent, or Firm* — Leydig, Voit & Mayer, Ltd.

(57) ABSTRACT

A method for suppressing a spurious pulse following a measurement pulse in a measurement signal using a circuit includes generating a square-wave signal from the measurement signal. A delayed square-wave signal is generated by delaying the square-wave signal by a time span $\tau_1$. The delayed square-wave signal is input into a control input of a switching arrangement. The measurement signal or a signal derived therefrom is input into an input of the switching arrangement. The signal at the input of the switching arrangement is switched to a first output of the switching arrangement based on the delayed first square-wave signal at the control input of the switching arrangement. The time span $\tau_1$ is matched to the measurement signal such that the switching arrangement is not switched to the first output during the spurious pulse. A signal at the first output is output as an output signal of the circuit.

15 Claims, 4 Drawing Sheets

CIRCUIT, SYSTEM AND METHOD FOR SUPPRESSING A SPURIOUS PULSE IN A MEASUREMENT SIGNAL

CROSS-REFERENCE TO PRIOR APPLICATION

Priority is claimed to Luxembourg Patent Application No. LU 93176, filed on Aug. 12, 2016, the entire disclosure of which is hereby incorporated by reference herein.

FIELD

The present invention relates to a circuit, a system and a method for suppressing a spurious pulse following a measurement pulse in a measurement signal. The present invention further relates to a microscope with a corresponding circuit.

BACKGROUND

In practice it is frequently necessary to detect a physical variable by means of a sensor or its detector and to generate a measurement signal representative of the physical variable. The electrical measurement signal arising therefrom is fed to an evaluation unit which suitably evaluates the measurement signal. The physical variable to be measured can be formed in a great variety of ways. Merely by way of example, reference is made to the field strength of a magnetic or electrical field, a separation, the intensity of a light beam or the arrival of a photon.

Some sensors tend to generate artifacts in the measurement signal. This relates, in particular, to sensors which generate a pulse-shaped measurement signal. The artifact or artifacts are then expressed in that one or more spurious pulses follow the actual measurement pulse. Herein, the spurious pulses can sometimes reach such large amplitudes that they can be confused with the actual measurement pulse. This is problematic particularly with sensor arrangements in which measurement pulses are to be counted since each spurious pulse can falsify the counter result.

Such a spurious pulse can have a variety of causes. Thus, sensors are known which, due to their measuring principle, tend toward so-called afterpulsing. These include, for example, SPAD (single photon avalanche diode) sensors. On the other hand, spurious pulses can be evoked by a connecting cable, for example, a coaxial cable on the signal path between the sensor and the evaluation unit. Herein, wave impedances of the individual components that are insufficiently matched to one another can lead to reflections on the signal path. Each change of the wave impedance generates a reflection site at which a measurement pulse is partially reflected. The spurious pulse then arises from reflected signal components. At the same time, each connecting cable has a capacitive and inductive covering. By this means, the sensor, the connecting cable and a possibly present preamplifier form an oscillating circuit which is excited into oscillation by the measurement pulse. Even if these oscillations are mostly severely damped in practice, the oscillation of this oscillating circuit can lead to spurious pulses with relatively large amplitudes. It is herein also possible that different causes of spurious pulses are overlaid.

In the case of sensors which tend toward afterpulsing, spurious pulses can be prevented in many cases by targeted driving of the detectors. A corresponding solution is disclosed, for example, in the article "SPAD Sensors Come of Age" by Edoardo Charbon and Silvano Donati in OPN Optics and Photonic News, February 2010. Therein, by means of targeted control of the biasing of the avalanche diode, afterpulsing is prevented or at least reduced. A disadvantage thereof is that such control is not always possible.

In the case of spurious pulses which are caused by changing wave impedances, in principle, the wave impedances of the individual components could be matched to one another. In practice, however, this is often not possible since it is possible only conditionally to exert an influence on the wave impedances. This procedure becomes particularly problematic if the impedance of a detector depends on its respective operating point. This is the case, for example, for photodiodes. The equivalent circuit diagram of a photodiode consists of a current source with an internal resistance and a parallel capacitance. The internal resistance changes dependent upon the irradiated light quantity. The impedance of the photodiode also changes therewith. Since the irradiated light quantity cannot be predicted, it is practically impossible in such a case to adapt the wave impedance of the connecting cable to the detector.

It is similarly problematic if the spurious pulses are evoked by the oscillation behavior of a connecting cable. Here there remains, if necessary, an additional damping of the oscillating circuit. However, this also leads to a damping of the actual measurement signal and to additional noise, so that this approach is usually ruled out in practice.

SUMMARY

In an embodiment, the present invention provides a circuit for suppressing a spurious pulse following a measurement pulse in a measurement signal. A binarizationer (also referred to herein as a binarization unit) is configured to generate a first square-wave signal from the measurement signal. A delayer (also referred to herein as a delay unit) is configured to delay a signal at an input of the delayer by a time span $\tau_1$ and to output the signal at an output of the delayer. A switching arrangement is configured, on the basis of a control signal at a control input of the switching arrangement, to switch a signal at an input of the switching arrangement to a first output of the switching arrangement. The circuit is arranged such that the first square-wave signal is applied as the signal at the input of the delayer, the first square-wave signal delayed by the delayer is applied as the control signal at the control input of the switching arrangement, the measurement signal or a signal derived from the measurement signal is applied as the signal at the input of the switching arrangement, and the first output of the switching arrangement forms an output of the circuit. The binarizationer is configured to generate the first square-wave signal such that the switching arrangement at least temporarily switches the signal at the input of the switching arrangement to the first output of the switching arrangement. The time span $\tau_1$ is matched to the measurement signal such that the switching arrangement is not switched to the first output of the switching arrangement during the spurious pulse.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
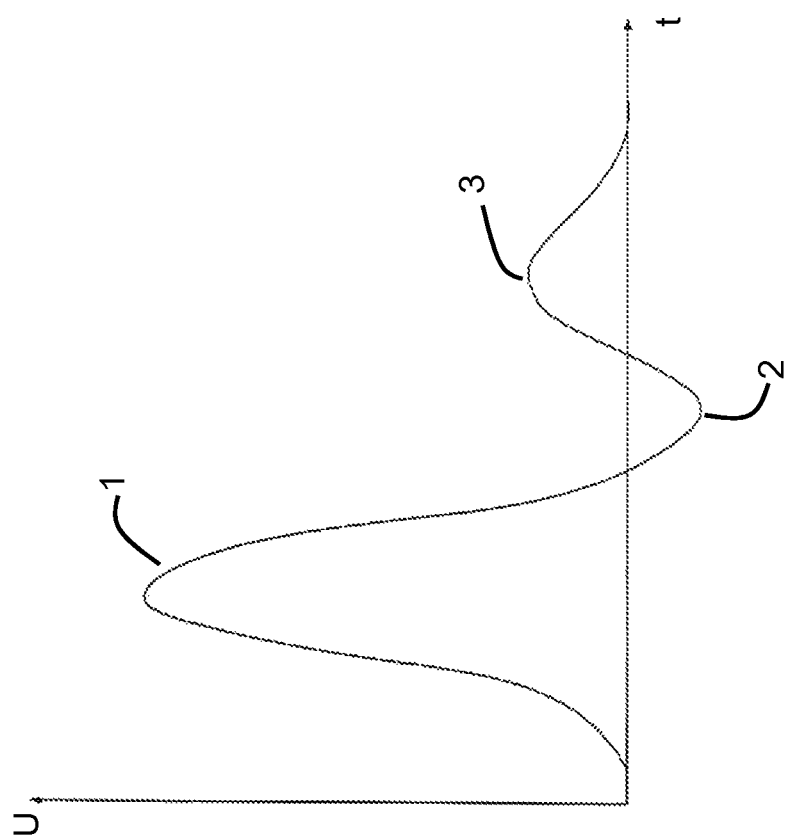
FIG. 1 is a graphical representation of an exemplary shape of a measurement signal with a measurement pulse and a spurious pulse following the measurement pulse.

An aspect of the present invention provides a circuit and a method with which a spurious pulse following the measurement pulse can be reliably suppressed or at least significantly reduced with simple means.

According to an embodiment of the present invention, the circuit with which a spurious pulse following the measurement pulse can be reliably suppressed or at least significantly reduced with simple means comprises:

a binarization unit which is configured to generate a first square-wave signal from the measurement signal, wherein the first square-wave signal adopts a first or a second level, a delay unit which is configured to delay a signal at an input of the delay unit by a time span $\tau_1$ and to output it at an output of the delay unit, and a switching arrangement which is configured, on the basis of a control signal at a control input of the switching arrangement, to switch a signal at an input of the switching arrangement to a first output of the control arrangement, wherein the first square-wave signal is applied to the input of the delay unit, wherein the first square-wave signal delayed by the delay unit is applied to the control input of the switching arrangement, wherein the measurement signal or a signal derived from the measurement signal is applied to the input of the switching arrangement, wherein the first output of the switching arrangement forms the output of the circuit, wherein the binarization unit generates the first square-wave signal such that the switching arrangement at least temporarily switches the signal existing at the input of the switching arrangement to the first output of the switching arrangement, and wherein the time span $\tau_1$ is matched to the measurement signal such that the switching arrangement is not switched to the first output of the switching arrangement during the spurious pulse.

According to another embodiment, a system with which a spurious pulse following the measurement pulse can be reliably suppressed or at least significantly reduced with simple means comprises:

a detector for generating a measurement signal, an inventive circuit wherein the measurement signal is applied to an input of the circuit, and an evaluation unit for evaluating the signal that is output by the circuit, wherein the output of the circuit is applied to an input of the evaluation unit.

According to a further embodiment, a microscope with which a spurious pulse following the measurement pulse can be reliably suppressed or at least significantly reduced with simple means, which is preferably configured as a fluorescence microscope, comprises:

a detector for generating a measurement signal, wherein the detector is configured for detecting detection light, in particular fluorescence light, from a sample examined by the microscope, an inventive circuit wherein the measurement signal is applied to an input of the circuit, and an evaluation unit for evaluating the signal that is output by the circuit, wherein the output of the circuit is applied to an input of the evaluation unit.

According to an even further embodiment, a method with which a spurious pulse following the measurement pulse can be reliably suppressed or at least significantly reduced with simple means comprises the steps:

generation of a first square-wave signal from the measurement signal by means of a binarization unit, generation of a delayed first square-wave signal by delaying the first square-wave signal by a time span $\tau_1$ by means of a delay unit, input of the delayed first square-wave signal into a control input of a switching arrangement, input of the measurement signal or a signal derived from the measurement signal into an input of the switching arrangement, at least temporary switching of the signal existing at the input of the switching arrangement to a first output of the switching arrangement on the basis of the delayed first square-wave signal existing at the control input of the switching arrangement, wherein the time span $\tau_1$ is matched to the measurement signal such that the switching arrangement is not switched to the first output of the switching arrangement during the spurious pulse, and output of a signal existing at the first output of the switching arrangement as the output signal.

In a manner according to embodiments of the invention, it was first recognized that a spurious pulse following a measurement pulse is typically in a largely constant temporal relationship to the measurement pulse. Regardless thereof by what the spurious pulse is triggered, a spurious pulse that is directly or indirectly attributable to the measurement pulse has a practically unchanging temporal position relative to the measurement pulse during a measuring cycle. The relative temporal position can depend on boundary conditions such as the temperature or a bias of the detector. However, these boundary conditions are usually largely constant during a measuring cycle, i.e. during a pre-defined number of successive measurement pulses, so that they have no appreciable effects on the temporal position of a spurious pulse relative to the respective measurement pulse. This very realization is used for the suppression of the spurious pulse in the measurement signal. For this purpose, according to the invention, a control signal is generated from the measurement signal which has a defined temporal position relative to the measurement signal and is used for removing the measurement signal at the time point of a spurious pulse.

The circuit according to an embodiment of the present invention, which implements this principle, comprises a binarization unit, a delay unit and a switching arrangement. The binarization unit generates a first square-wave signal from the measurement signal, the temporal shape of which is in a defined relationship to the measurement signal. Thus the first square-wave signal can have, for example, a flank when the measurement signal exceeds or falls below a pre-defined level. This first square-wave signal is input into the delay unit which delays the first square-wave signal by a time span $\tau_1$ in a defined manner and thereby generates a delayed first square-wave signal. The delayed first square-wave signal is input into a control input of the switching arrangement as a control signal. The measurement signal is input into the (signal) input of the switching arrangement. The switching arrangement switches—on the basis of the control signal at the control input—the signal existing at the input of the switching arrangement to a first output or separates the input of the switching arrangement from the first output. The first output of the switching arrangement forms an output of the circuit.

The switching arrangement can herein be level-controlled or edge-controlled. A level-controlled switching arrangement carries out a switching event whenever a particular level is undershot or exceeded at the control input. Thus, for example, at a high level (for example 5 V) at the control input of the input to the switching arrangement, it is possible to switch to the first output, whilst at a low level (for example 0 V), no conductive connection exists between the input of the switching arrangement and the first output. An edge-controlled switching arrangement always carries out a switching event if a rising and/or a falling flank is detected. Thus, both the measurement pulse and also the spurious pulse can evoke a rising flank in the delayed first square-wave signal. The delayed rising flank of the measurement pulse can then trigger, for example, a first switching event and the delayed rising flank of the spurious pulse can trigger a second switching event.

In both cases (level-controlled or edge-controlled), the binarization unit generates the first square-wave signal such that the switching arrangement at least temporarily switches the signal existing at the input of the switching arrangement to the first output of the switching arrangement. On the other hand, this means also that the signal existing at the input of the switching arrangement is at least temporarily not switched to the first output of the switching arrangement. Through a suitable choice of the time span $\tau_1$, the duration in which no conductive connection exists between the input of the switching arrangement and the first output of the switching arrangement can be regulated such that at the time point of the spurious pulse, the measurement signal is not switched to the first output.

As previously stated, a measurement pulse and a spurious pulse following the measurement pulse usually have a largely constant temporal relationship to one another. This temporal relationship is defined by the measuring system (and is thus known) or can be easily determined in an actual measuring system by calibration measurements. In this way, a time span $\tau_1$ can be easily determined and specified by means of which a spurious pulse can be suppressed with the inventive circuit. In this way, with a simple circuit effort, a circuit can be produced which can suppress the spurious pulse following a measurement pulse. It is herein largely immaterial for the functioning how the spurious pulse has arisen, provided it has a largely defined temporal relationship to the measurement pulse. Herein, the temporal relationship does not even have to be entirely constant, provided the spurious pulse to be suppressed lies within a pre-definable time window. In this way, an extremely flexibly usable circuit comes into being.

The first square-wave signal can in principle be formed in a variety of ways. Typically, the first square-wave signal assumes a first level or a second level or changes from the first level to the second level or vice versa. At what actual values the first level and the second level are selected and what significance the levels have for the switching arrangement depends on the respective switching arrangement. Herein, the first square-wave signal can be configured as a unipolar or a bipolar square-wave signal. In a unipolar square-wave signal, the first level and the second level do not have different signs. Thus, one of the two levels has a positive or a negative value, whereas the other of the two levels is present either at a ground potential (0 V) or at another value with the same sign. It is therefore conceivable that the first level lies at 3.3 V and the second at 0 V. It is also conceivable, for example, that the first level is 1.5 V and the second 5 V. For negative levels, it is conceivable that the first level is −5 V and the second −3.3 V. In the case of a bipolar square-wave signal, the first level has a different sign to that of the second level. In practice, the values of the two levels are often the same. Thus the first level can be, for example +2.5 V and the second level −2.5 V.

The first square-wave signal can be transmitted relative to a ground potential or the first square-wave signal can be formed as a differential signal. The latter has become established, in particular, in rapid digital transmissions. For differential signals, levels are used which are different from 0 V. Differential signals are usually utilized with corresponding logic standards, such as for example, LVDS (low voltage differential signaling), CML (current mode logic) or (P)ECL ((positive) emitter-coupled logic).

For the functioning of the inventive circuit, it is largely unimportant how a measurement pulse actually looks and by which sensor/detector it has been generated. It is important only that the measurement pulse can be converted in a defined manner into a first square-wave signal. For this purpose, it is usually sufficient that the measurement pulse has an adequately defined temporal sequence, i.e. the measurement pulse must be sufficiently separated from the noise in the measurement signal. However, this is a requirement which is to be placed on most measurement signals in any event, in order to be able to guarantee the processing capability of the measurement signal by an evaluation unit. It is not decisive whether a measurement pulse is configured as a square-wave pulse, as a Gaussian bell curve or as a sinusoidal oscillation, to name merely a few examples. Furthermore, the measurement pulses should have a sufficiently large separation from one another within the measurement signal, so that a measurement pulse is not overlaid with a spurious pulse. In practice, however, this is not an actual restriction.

The circuit can be implemented in a great variety of ways. The circuit can be realized with discrete components, integrated circuits or a combination of both. Insofar as the temporal separations with which measurement pulses and spurious pulses follow one another permit, programmable components are preferably used. For this purpose, by way of example, reference is made to the use of FPGAs (field programmable gate arrays) or suitably programmed processors such as DSPs (digital signal processors). If the temporal spacings between measurement pulses and spurious pulses fall below a particular threshold, for example, below 5 ns, rapid digital logic components are preferably used. For example, superfast comparators or D flip-flops are known which can process signal rates up to the GHz range and have time delays of less than 200 ps. Such integrated circuits can be put to good use in the implementation of the inventive circuit. By means also of ASICs (application specific integrated circuits), corresponding processing speeds can be realized.

If, for the further processing of the measurement pulse, the respective exact voltage or current value of the measurement signal is not important, then a signal derived from the measurement pulse can also be used. This is the case, for example, in arrangements in which the number of measurement pulses within a time span is to be determined. In this or similar cases, only the time point of a measurement pulse or usually even only the number of pulses during a predetermined time span is of interest, whilst the actual size of the measurement pulse and the actual shape of the rising phase and the falling phase of the measurement signal are relatively unimportant. Here, the measurement signal could also be converted into a square-wave signal and by this means a signal derived from the measurement signal could form. In such an arrangement, the signal derived from the measurement signal would be input into the switching arrangement. By this means, a signal derived from the measurement signal in which the spurious pulse or spurious pulses is/are removed would exist at the first output of the switching arrangement and/or at the output of the circuit.

In a preferred embodiment of such a signal derived from the measurement signal, the derived signal could be a second square-wave signal. This can be useful, for example, if the time point of a measurement pulse is crucially important for the evaluation of the measurement signal. Through the conversion into a square-wave signal, defined and marked level changes take place which are simply evaluable by an evaluation unit. Preferably, such a second square-wave signal is generated by the binarization unit in addition to the first square-wave signal.

In a preferred embodiment, the binarization unit is formed by a comparator which is configured as a threshold switch. In a first input of the comparator, the measurement signal would be input whilst at a second input a reference voltage—the first threshold value—is applied. If the measurement signal at the first input exceeds the value of the reference voltage at the second input, then the output of the comparator would assume a first level. If the measurement signal falls below the reference voltage, a second level would be output. Precisely how the first and second levels look depends on the wiring and the design of the comparator. As a result, therefore, the comparator would compare the measurement signal with a first threshold and generate a binarized output signal which depends on the level of the measurement signal.

If the binarization unit generates both the first and also the second square-wave signal, the binarization unit can also be configured in a variety of ways. In a first embodiment, the binarization unit has a splitter which generates the first and the second square-wave signal from an output signal of a comparator. The comparator configured as a threshold switch would generate a square-wave signal which is duplicated by the splitter and is output as a first and second square-wave signal. This embodiment offers the advantage that the two square-wave signals will have an approximately identical temporal behavior. Furthermore, a splitter is simply realizable with circuit technology.

In a second embodiment, the binarization unit can have two comparators, each configured as a threshold switch. Herein, a first comparator would compare the measurement signal with a first threshold and generate and output the first square-wave signal. Accordingly, the second comparator would compare the measurement signal with a second threshold and generate and output the second square-wave signal. In this way, the first square-wave signal can be generated independently of the second square-wave signal. Herein, the first threshold can be selected to be the same as the second threshold, so that the first square-wave signal will be largely identical to the second square-wave signal. It is, however, also conceivable that the first threshold is larger or smaller than the second threshold. By this means, a rising flank in the first square-wave signal would occur later or earlier than in the second square-wave signal. A falling flank would then lie earlier or later in the first square-wave signal than in the second square-wave signal. In this way, particular requirements can be specifically adopted in the generation of the two square-wave signals. This embodiment therefore offers greater flexibility in the generation of the first and second square-wave signals.

In a preferred embodiment of the switching arrangement, in addition to a first output, it also has a second output. A switching arrangement of this type would switch a signal existing at the input of the switching arrangement to the first or the second output. In this development, also, the switching processes would take place on the basis of the control signal which is applied to the control input of the switching arrangement. Herein, a switching process would mean that the switching arrangement breaks a conductive connection between the input and the first/second output and substantially simultaneously creates a conductive connection between the input and the second/first input of the switching arrangement.

In this embodiment, the second output can be used variously. It is thus conceivable that the second output is connected to a terminating resistor. In this way, the measurement signal or the signal derived from the measurement signal would either be output at the first output of the switching arrangement and thus to the output of the circuit or would be terminated in a defined way by the terminating resistor. By this means, signal reflections can be effectively prevented in the case of an open connection between the input of the switching arrangement and the first output. It is, however, also conceivable that the second output is input into an evaluation unit. If a voltage not equal to 0 V exists at the second output, then the measurement signal or the signal derived from the measurement signal is not output at the output of the circuit. The signal at the second output is therefore approximately the inverse of the signal at the first output and can be used for the evaluation of suppressed spurious pulses. Thus, for example, a counting of rising flanks at the second output is conceivable in order to determine the number of suppressed spurious pulses.

In the configuration of the switching arrangement with a first and a second output, the switching arrangement can be configured level-controlled. Herein, on application of a first level at the control input, a signal at the input of the switching arrangement would be switched to the first output. On application of a second level at the control input, a signal at the input of the switching arrangement would be switched to the second output. A configuration of this type offers the advantage that a level-controlled switching arrangement can be very easily implemented by means of transistors.

In another embodiment of this switching arrangement, it is edge-controlled, i.e. on occurrence of a rising and/or falling flank of the delayed first square-wave signal, the "switch position" of the switching arrangement changes between the first output and the second output or vice versa. If, for example, a rising flank triggers a switching event in each case, a rising flank which originates from the start of a measurement pulse would trigger a first switching event with a time delay of $\tau_1$. A rising flank which originates from the start of the spurious pulse would trigger a second switching event with a time delay of $\tau_1$. In this way, the temporal spacing between the measurement pulse and the spurious pulse has an influence on the behavior of the switching arrangement.

In principle, the switching arrangement can be implemented in a variety of ways. Preferably, however, electronic switches are used since they switch without wear (or at least low wear) and permit higher switching frequencies than mechanical switches. In a particularly preferred manner, transistors, in particular MOSFETs (metal oxide semiconductor field effect transistors) are used. Provided the switching arrangement has only one first output, the electronic switch would open or close the connection between the input and the first output, based upon the control signal. Provided the switching arrangement has a first and a second output, for each of the outputs an electronic switch can be provided, being controlled with an inverted control signal. In this way, one switch would open and the other switch would close in each case. Corresponding switching arrangements are known in practice.

Provided the evaluation of the measurement signal that is processed by the inventive circuit does not rely upon the actual amplitude of the measurement pulse, but that digital values suffice (for example, a threshold is exceeded or is not undershot), the switch could also be formed by a digital circuit. In this regard, reference is made to a digital multiplexer as a preferred exemplary embodiment. The control input of the switching arrangement is then provided by the control input of the digital multiplexer.

For better adaptability to different measurement signals, the delay unit can be configured adaptable. Herein, firstly the time span $\tau_1$ can be settable, by which means the extent of the delay of the first square-wave signal can be varied. Secondly, a duration $\tau_2$ can be settable wherein the duration $\tau_2$ gives the spacing between a rising flank and a falling flank of the delayed first square-wave signal. By setting the duration $\tau_2$, the "width" of the control signal for the switching arrangement can be varied. The longer the duration $\tau_2$ is selected to be, the longer the measurement signal or the signal derived from the measurement signal will not be switched to the first output of the switching arrangement.

The durations $\tau_1$ and $\tau_2$ can herein be set in a great variety of ways. In particular, in the implementation of the circuit or the delay unit by means of a programmable component, the durations can be firmly programmed in during calibration measurements. At the same time, an operator can be given the possibility of adapting the durations by means of a control computer. Additionally or alternatively, it is also possible that the durations are automatically adapted based upon further measurement variables. If, for example, it is known that a detector used evokes a spurious pulse, the temporal spacing of which from the measurement pulse depends on the bias at the detector, then a measurement value can be used for the bias for an automatic adaptation of the durations $\tau_1$ and $\tau_2$.

In a particularly simple embodiment, a delay unit adaptable in this way can be formed by a D flip-flop and two adjustable delay elements. The first square-wave signal would be applied to an input of the first delay element. The signal delayed by the first delay element would then be applied to an input of the second delay element and a clock input of the D flip-flop. The signal further delayed by the second delay element would be applied as the reset signal to the reset input of the D flip-flop. The output of the D flip-flop would form the output of the delay unit. Thus the first delay element would define the time span $\tau_1$, whilst the second delay element sets the duration $\tau_2$.

The inventive circuit preferably comes into use in a system with a detector, which generates a corresponding measurement signal with a plurality of successive measurement pulses. Each of these measurement pulses would be followed by a—more or less pronounced—spurious pulse. The system also comprises an evaluation unit to which a cleaned-up signal is fed by the inventive circuit for evaluation.

Herein, a system of this type is formed in a particularly preferred embodiment by a microscope and comprises a detector, an inventive circuit and an evaluation unit for evaluating the signal output by the circuit. The detector is configured to detect the detection light emerging from the sample under investigation. Preferably, the detector can detect individual photons of the detection light and can be formed, for example, by a SPAD sensor, a photomultiplier tube or a hybrid sensor with a photocathode, a high voltage acceleration path and an avalanche diode. In the case of a detector which can detect individual photons, the evaluation unit would preferably be configured to count the pulses in the prepared measurement signal. An evaluation unit of this type could thus count the photons received by the detector.

The microscope is preferably a fluorescence microscope, i.e. a microscope in which a light beam (usually a laser beam) excites a fluorescing sample under examination to emit fluorescence light and the fluorescence light is detected. The detector would thus detect fluorescence light as the detection light.

FIG. 1 shows a graphical representation of an exemplary shape of a measurement signal which can be processed by the inventive circuit. Such a measurement signal is generated, for example, by a hybrid detector consisting of a photocathode, a high voltage acceleration path and an avalanche diode with a downstream-connected amplifier and a connection cable.

In the graph of FIG. 1, a voltage is plotted against time. In the measurement signal represented, a measurement pulse 1 is followed by an undershoot 2 and a spurious pulse 3. Thereafter, the measurement signal has a voltage approaching 0 V. The curve clearly shows the behavior of a strongly damped oscillating circuit. In a sensor which was used in a test set-up, typical pulse heights were between 100 mV and 2 V, dependent upon the circuit actually used. The width of the measurement pulse (the time with a voltage above 40% of the maximum) is typically 500 ps to 20 ns. The spurious pulse typically follows with a delay of 1 ns to 5 ns after the measurement pulse, wherein in practice the temporal separation varies by less than 100 ps. The height of the spurious pulse is typically 10% to 30% of the preceding measurement pulse. The noise level is typically less than 5% of the height of the measurement pulse. It should be expressly noted that these numerical values are given purely to illustrate the behavior of the inventive system. This description should not be understood as a restriction either to these numerical values, or to a particular sensor or sensor type.

Figure 2:
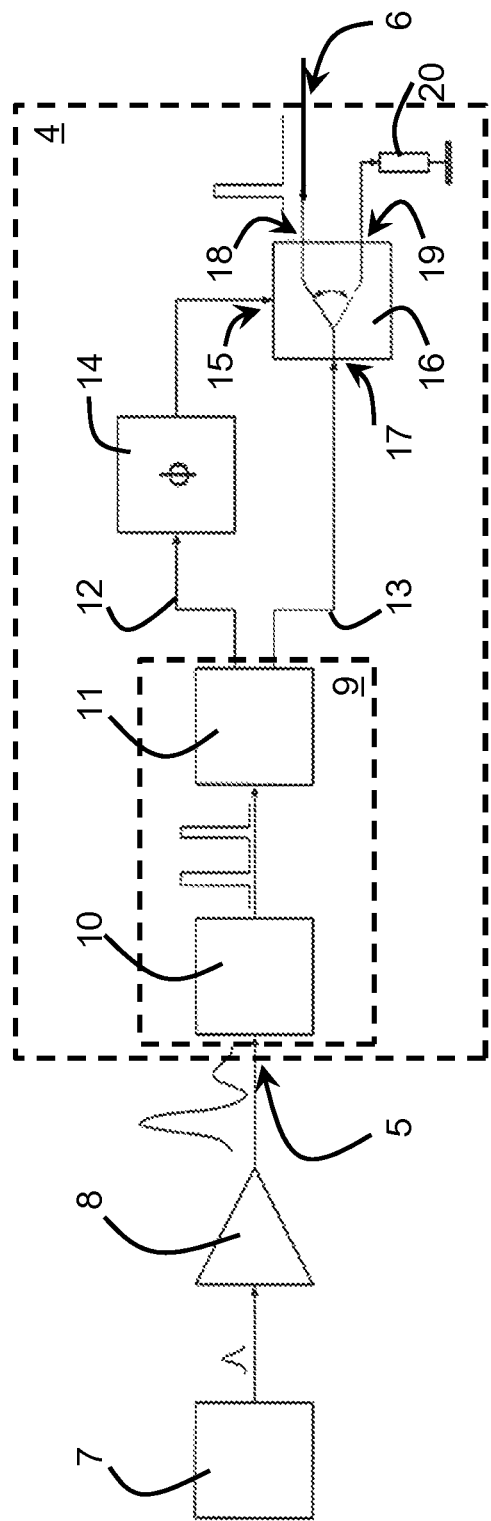
FIG. 2 is a block circuit diagram of an exemplary embodiment of a circuit in accordance with the present invention.

FIG. 2 shows an exemplary embodiment of an inventive circuit 4. The circuit 4 has an input 5 and an output 6. A measurement signal which is generated by a detector 7 and is amplified by an amplifier 8 is input into the input 5 of the circuit 4. A connecting cable arranged between the amplifier 8 and the input 5 of the circuit 4, which is reproduced simplified here merely as a line, forms an oscillating circuit which causes a measurement signal according to FIG. 1 to form from the amplified signal from the detector 7.

This measurement signal fed into the input of the circuit is applied to a binarization unit 9 which converts the measurement signal into a first square-wave signal and a second square-wave signal. The binarization unit 9 itself consists of a comparator 10 which is wired as a threshold switch, and a splitter 11. The comparator 10 generates a high level at its output when the voltage input into the comparator 10—in the present case, the measurement signal—exceeds a reference voltage. In all other cases, a low level is output. The reference voltage is herein set to a value of between 10% and 30% of the maximum pulse height to be expected. This square-wave signal generated by the comparator 10 is fed to the splitter 11 which duplicates the square-wave signal and outputs it as a first square-wave signal to the line 12 and as a second square-wave signal to the line 13.

The first square-wave signal is applied to a delay unit 14 which delays the input signal by a time span $\tau_1$. In a preferred embodiment which is considered in more detail in relation to FIG. 3, apart from a delay, the width of the input square-wave signal is also influenced and is set to a duration of $\tau_2$. In this way, a signal designated generally as a "delayed first square-wave signal" comes about. This delayed first square-wave signal is input into a control input 15 of a switching arrangement 16.

Apart from the control input 15, the switching arrangement 16 also has a (signal) input 17, a first output 18 and a second output 19. In the input 17, the second square-wave signal applied to the line 13 is input as a signal derived from the measurement signal. This signal is switched dependent upon the control signal input at the control input 15 to the first output 18 or the second output 19. Herein, the switching arrangement 16 is level-controlled so that given a low level at the control input 15, the input 17 is switched to the first output 18 and given a high level at the control input 15, the input 17 is switched to the second output 19. The first output 18 simultaneously forms the output 6 of the circuit 4. The second output 19 in this exemplary embodiment is connected via a terminating resistor 20 to ground, so that the measurement signal experiences a defined resistance on output via the second output 19. The output 6 of the circuit is connected to an evaluation unit.

Figure 3:
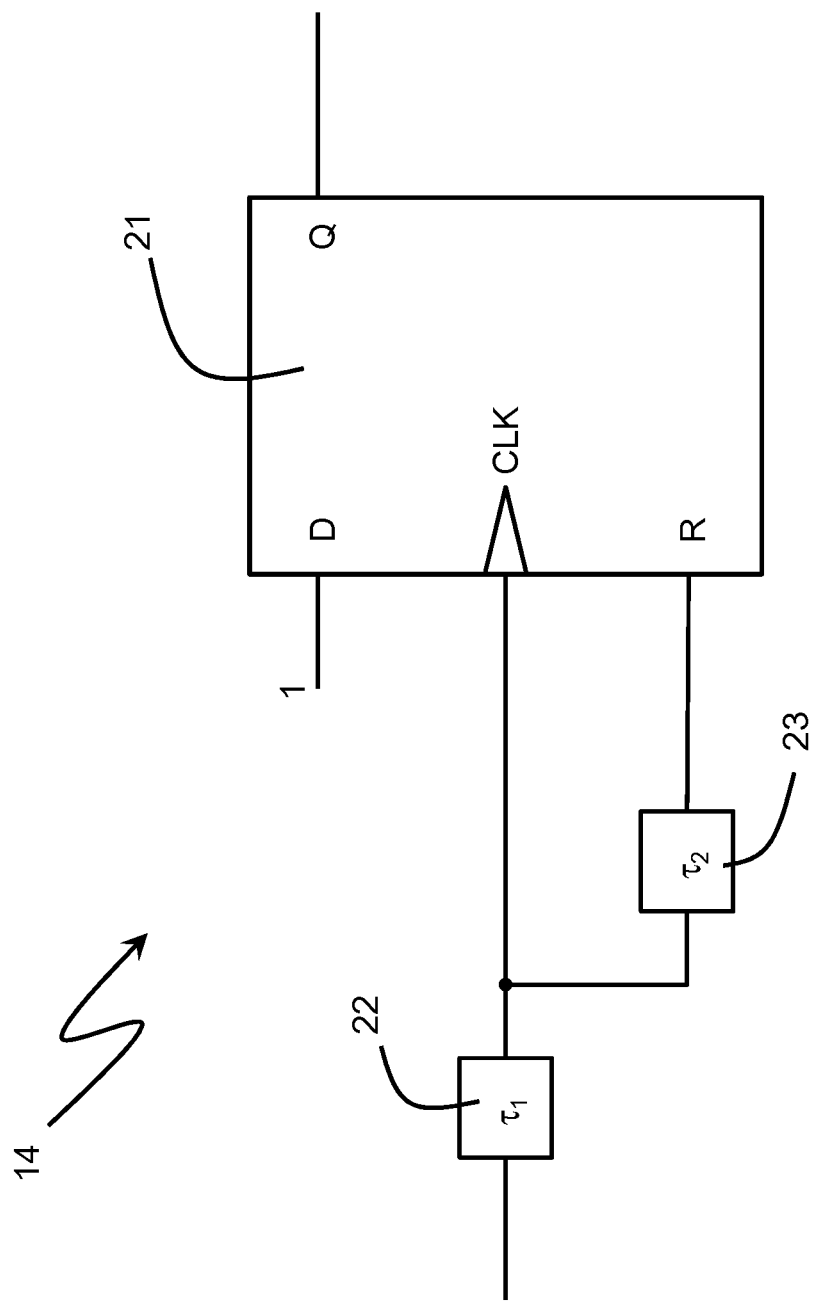
FIG. 3 is a block circuit diagram of an embodiment of a delay unit in the inventive circuit according to FIG. 2.

FIG. 3 shows an exemplary embodiment of a delay unit 14 as it can be used in the inventive circuit 4. The delay unit 14 comprises a D flip-flop 21 and a first and a second delay element 22, 23. The signal to be delayed is input into the first delay element 22 which delays the input signal by a time span $\tau_1$ and outputs the delayed signal. This delayed signal is input to a clock input of the D flip-flop 21 and to the second delay element 23. The second delay element delays the signal further by a duration $\tau_2$ and outputs the further delayed signal to a reset input of the D flip-flop 21. Applied to the D input of the D flip-flop is a high level which is identified, for simplicity, with a "1" at the D input.

If a signal that is input into the delay unit 14 has a rising flank, this rising flank is delayed by the first delay element 22 by a time span $\tau_1$. Through input into the clock input of the D flip-flop, the signal at the Q output is set to a high level by the delayed rising flank. The signal delayed by the time span $\tau_1$ is further delayed by the second delay element and after a duration $\tau_2$, sets the signal at the Q output to a low level again. If the rising flank is to take place at the time point $t_0$, the signal at the output of the delay unit (Q output of the D flip-flop) has a rising flank at the time point $t_0+\tau_1$. At the time point $t_0+\tau_1+\tau_2$, a high level then lies at the output. Following this time point, the delayed signal is again set to a low level.

The embodiment of the delay unit shown in FIG. 3 has the advantage, in addition to the influencing capability of the delay and the width of the delayed pulse, that until the resetting at the time point $t_0+\tau_1+\tau_2$, it is "blind" to new rising flanks. By this means, a further rising flank possibly generated by a spurious signal has no influence on a switching event in the switching arrangement.

Figure 4:
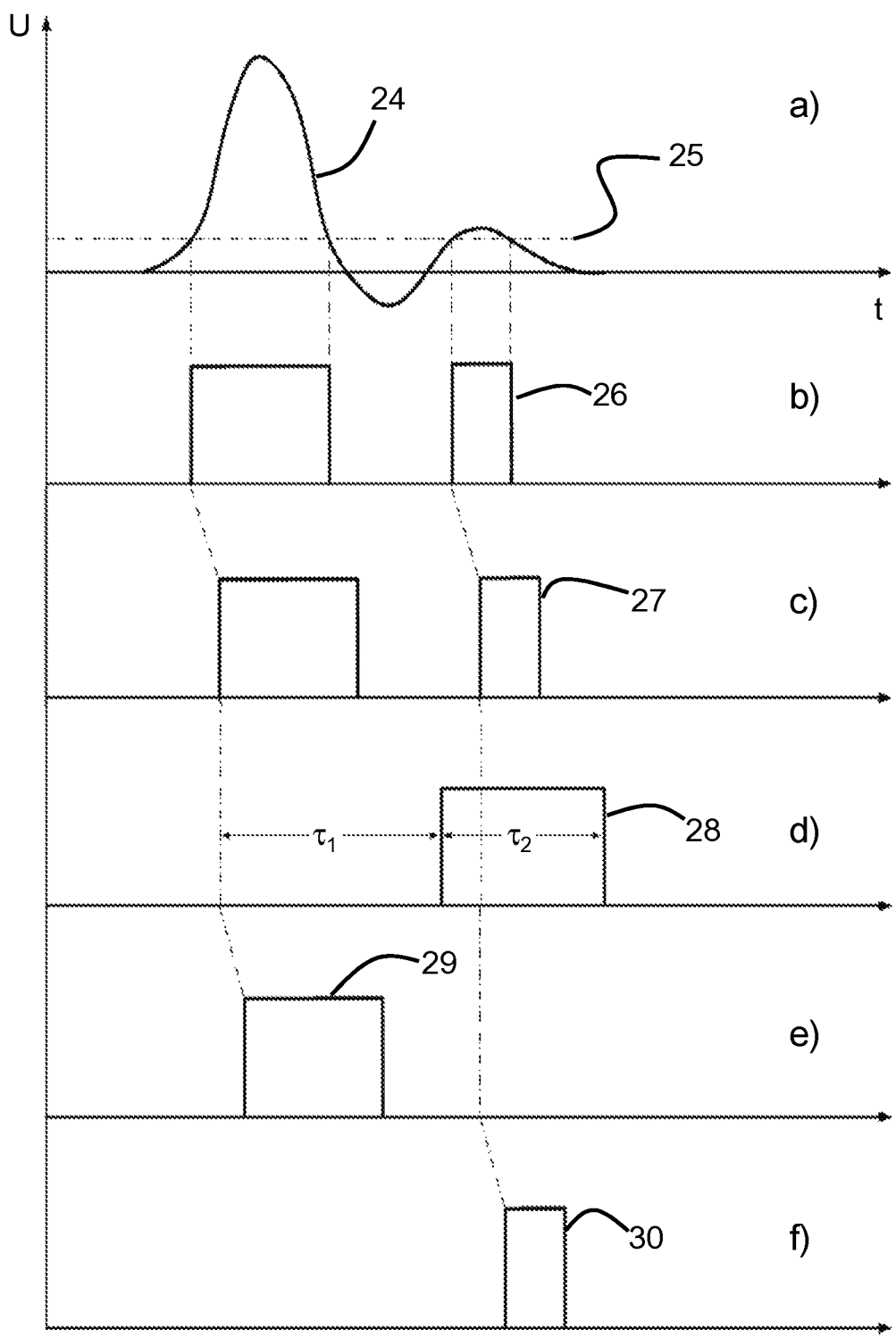
FIG. 4 shows graphical representations of exemplary signal sequences in the inventive circuit of FIG. 2.

FIG. 4 shows graphical representations with exemplary signal sequences, as can arise in the circuit according to FIG. 2. In this context, the cooperation of the individual elements of the circuit of FIG. 2 will be considered again in more detail. In each of the graphs, a voltage U is plotted against time t. Herein, the individual time axes each relate to a common reference time point. Correspondences of flanks of the signals are shown by dashed lines between the individual graphs.

The partial FIG. 4a) (i.e. part a) of FIG. 4) shows, by way of example, the shape of a measurement signal 24 which is already shown in FIG. 1. In addition, a comparator threshold value 25 is drawn in as a horizontal line which is input into the comparator 10 in addition to the measurement signal 24 as a comparison value. This comparator threshold value 25 is the first threshold value as mentioned in the accompanying claims. If the measurement signal 24 at the input 5 of the circuit 4 (and thus at the input of the binarization unit 9) exceeds the comparator threshold value 25, the binarized signal output by the comparator 10 assumes a high level. If the measurement signal 24 at the input 5 of the circuit 1 lies below this threshold value 24, the comparator 10 outputs a low level. A correspondingly binarized signal 26, as is output by the comparator 10, is shown in partial FIG. 4b).

Partial FIG. 4c) shows the associated pattern of the first square-wave signal 27 which is input into the input 17 of the switching arrangement 16. Since in the circuit of FIG. 2, the first square-wave signal 27 is generated by a splitter 11 from the binarized signal 26, the pattern shown in partial FIG. 4c) represents the signal shape of the second square-wave signal. By means of the signal transit times through the splitter 11 and the transit times on the connecting lines between the individual components of the circuit, a slight delay comes about, which results in a displacement of the rising and falling flanks. For the sake of clarity, the time delay is shown relatively distinctly in FIG. 4.

In partial FIG. 4d), an exemplary pattern of a delayed first square-wave signal 28 is shown, as could be output by the delay unit 14. The delayed first square-wave signal 28 is delayed by the time span $\tau_1$. In addition, in this example, the delay unit 14 has increased the temporal spacing between the rising and falling flanks to a duration $\tau_2$. Such a behavior is shown, for example, by the circuit of FIG. 3.

The second square-wave signal (according to partial FIG. 4c)) is input into the signal input of the switching arrangement 16. The delayed first square-wave signal 28 forms the control signal for the switching arrangement 16 and is input into the control input 15. The partial FIGS. 4e) and 4f) show the signal pattern arising therefrom at the outputs of the switching arrangement 16. Partial FIG. 4e) shows a signal 29 at the first output 18 and partial FIG. 4f) shows a signal 30 at the second output 19. Here also, the signal transit times through the switching arrangement lead to a time delay which leads to a corresponding temporal offset. This is made clear by an offset vertical line.

From the individual partial figures, it is apparent that the time span $\tau_1$ is dimensioned such that the delayed first square-wave signal lies at a high level at the time point of the spurious pulse. Since the switching arrangement 16 switches the input 17 to the second output 19 on application of a high level at the control input 15, the switching arrangement 16 is not switched to the first output 18 during the spurious pulse. Conversely—in the embodiment shown here—at all other time points, the input 17 of the switching arrangement 16 is switched to the first output 18. The signal from the first output forms the output signal of the circuit and is emitted at the output 6. It should be recognized that this output signal contains only one signal component which depends on the measurement pulse 1. Specifically, the output signal always assumes a high level if the measurement signal 24 has exceeded the comparator threshold value 25. If, for example, the measurement signal always contains a measurement pulse when the detector generating the measurement signal detects a photon, then by counting the rising flanks, the number of detected photons can be determined. Since the circuit 4 has a deterministic time behavior, from the signal 29, even the time point of the reception can be determined relatively precisely. Since the time behavior of the circuit 4 practically does not change it is also possible to count very precisely how many photons are received per time unit.

Finally, reference is expressly made thereto that the above-described exemplary embodiments of the inventive circuit serve merely to explain the claimed teaching, although without restricting it to the exemplary embodiments. In particular, all the features contained in this description and/or their functions, effects and properties considered individually and/or in combination with one another which a person skilled in the art active in the present field would provide for solving the objective problem or problems associated therewith, making use where relevant, of his specialist knowledge, should be regarded as disclosed herein.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A circuit for suppressing a spurious pulse following a measurement pulse in a measurement signal, the circuit comprising
  a binarizationer configured to generate a first square-wave signal from the measurement signal;
  a delayer configured to delay a signal at an input of the delayer by a time span $\tau_1$ and to output the signal at an output of the delayer; and
  a switching arrangement configured, on the basis of a control signal at a control input of the switching arrangement, to switch a signal at an input of the switching arrangement to a first output of the switching arrangement;
  wherein the circuit is arranged such that the first square-wave signal is applied as the signal at the input of the delayer, the first square-wave signal delayed by the delayer is applied as the control signal at the control input of the switching arrangement, the measurement signal or a signal derived from the measurement signal is applied as the signal at the input of the switching arrangement, and the first output of the switching arrangement forms an output of the circuit,
  wherein the binarizationer is configured to generate the first square-wave signal such that the switching arrangement at least temporarily switches the signal at the input of the switching arrangement to the first output of the switching arrangement, and
  wherein the time span $\tau_1$ is matched to the measurement signal such that the switching arrangement is not switched to the first output of the switching arrangement during the spurious pulse.

2. The circuit as claimed in claim 1, wherein the binarizationer is configured to generate a second square-wave signal from the measurement signal and to output the second square-wave signal as the signal derived from the measurement signal.

3. The circuit as claimed in claim 1, wherein the binarizationer comprises a comparator configured as a threshold switch and operable to compare the measurement signal with a first threshold.

4. The circuit as claimed in claim 2, wherein the binarizationer comprises a splitter which is configured to generate the first and second square-wave signal from an output signal of a comparator of the binarizationer configured as a threshold switch and operable to compare the measurement signal with a first threshold.

5. The circuit as claimed in claim 2, wherein the binarizationer comprises a first and a second comparator which are each configured as a threshold switch and operable to compare the measurement signal with a first and a second threshold, respectively, wherein the first comparator generates and outputs the first square-wave signal and the second comparator generates and outputs the second square-wave signal.

6. The circuit as claimed in claim 1, wherein the switching arrangement comprises a second output, and wherein the switching arrangement is configured to switch the signal at the input of the switching arrangement to the first or the second output based on the control signal at the control input.

7. The circuit as claimed in claim 6, wherein the switching arrangement is configured such that, on application of a first level to the control input, the switching arrangement switches the input to the first output, and such that, on application of a second level to the control input, the switching arrangement switches the input to the second output.

8. The circuit as claimed in claim 6, wherein the switching arrangement is edge-controlled such that the switching arrangement changes, on occurrence of a rising or falling flank of the first square-wave signal at the control input, between the first and the second output.

9. The circuit as claimed in claim 1, wherein the switching arrangement is an electronic switch.

10. The circuit as claimed in claim 1, wherein the delayer is configured such that the time span $\tau_1$ and/or a duration $\tau_2$ between a rising flank and a falling flank of the delayed first square-wave signal is adjustable.

11. The circuit as claimed in claim 10, wherein the delayer comprises a D flip-flop and a first and a second delay element, wherein the first square-wave signal is applied to an input of the first delay element, wherein the signal delayed by the first delay element is applied to an input of the second delay element and a clock input of the D flip-flop, and wherein the signal delayed by the second delay element is applied to a reset input of the D flip-flop.

12. A system for suppressing a spurious pulse following a measurement pulse in a measurement signal, the system comprising:

a detector configured to generate the measurement signal;

a circuit as claimed in claim 1, wherein the measurement signal is applied to an input of the circuit; and an evaluator configured to evaluate the signal that is output by the circuit, wherein the output of the circuit is applied to an input of the evaluator.

13. A microscope, comprising:

a detector configured to detect detection light from a sample under examination by the microscope and to generate the measurement signal;

a circuit as claimed in claim 1, wherein the measurement signal is applied to an input of the circuit; and an evaluator configured to evaluate the signal that is output by the circuit, wherein the output of the circuit is applied to an input of the evaluator.

14. The microscope as claimed in claim 13, wherein the detector is configured to detect individual photons of the detection light, and wherein the evaluator is configured to count pulses in the measurement signal and to thereby count the photons received by the detector.

15. A method for suppressing a spurious pulse following a measurement pulse in a measurement signal using a circuit, the method comprising:

generating a first square-wave signal from the measurement signal;

generating a delayed first square-wave signal by delaying the first square-wave signal by a time span $\tau_1$;

inputting the delayed first square-wave signal into a control input of a switching arrangement;

inputting the measurement signal or a signal derived from the measurement signal into an input of the switching arrangement;

at least temporary switching the signal at the input of the switching arrangement to a first output of the switching arrangement based on the delayed first square-wave signal at the control input of the switching arrangement, wherein the time span $\tau_1$ is matched to the measurement signal such that the switching arrangement is not switched to the first output of the switching arrangement during the spurious pulse; and outputting a signal at the first output of the switching arrangement as an output signal of the circuit.

* * * * *